(12) United States Patent
Christensen

(10) Patent No.: US 8,282,613 B2
(45) Date of Patent: Oct. 9, 2012

(54) DISPOSABLE URINE BAG FOR COLLECTING URINE

(75) Inventor: Bjarne Lasse Christensen, Køge (DK)

(73) Assignee: Unomedical A/S, Birkeroed (DK)

( * ) Notice: Subject to any disclaimer, the term of this patent is extended or adjusted under 35 U.S.C. 154(b) by 568 days.

(21) Appl. No.: 10/546,888

(22) PCT Filed: Feb. 26, 2004

(86) PCT No.: PCT/DK2004/000128
§ 371 (c)(1), (2), (4) Date: Jun. 26, 2006

(87) PCT Pub. No.: WO2004/075795
PCT Pub. Date: Sep. 10, 2004

(65) Prior Publication Data
US 2007/0149934 A1    Jun. 28, 2007

(30) Foreign Application Priority Data
Feb. 27, 2003 (DK) .................................. 2003 00307

(51) Int. Cl.
*A61F 5/44* (2006.01)
*A61M 1/00* (2006.01)
*A61M 27/00* (2006.01)
*A61M 25/16* (2006.01)
*A61M 25/18* (2006.01)
*A61M 39/00* (2006.01)
*A61M 39/10* (2006.01)
*F16K 17/14* (2006.01)
*F16K 17/40* (2006.01)
*F16K 5/06* (2006.01)
*B65D 33/00* (2006.01)

(52) U.S. Cl. ........ 604/349; 604/540; 604/544; 604/317; 604/533; 137/67; 137/68.11; 137/68.19; 137/797; 383/210

(58) Field of Classification Search .................. 604/540, 604/544, 317, 327, 411, 523, 533, 905; 137/67, 137/68.11, 68.19, 797; 383/210; 285/3; 222/541.1
See application file for complete search history.

(56) References Cited

U.S. PATENT DOCUMENTS
2,883,985 A    4/1959 Evans
(Continued)

FOREIGN PATENT DOCUMENTS
EP    0 711 536 A1    5/1996
(Continued)

OTHER PUBLICATIONS

Yourdictionary.com—dictionary definition of "concentric" http://www.yourdictionary.com/concentric accessed Monday, Apr. 2, 2012.*

(Continued)

*Primary Examiner* — Tatyana Zalukaeva
*Assistant Examiner* — Adam Marcetich
(74) *Attorney, Agent, or Firm* — Brinks Hofer Gilson & Lione

(57) ABSTRACT

A disposable urine bag is provided. The bag includes an upper delimiting edge, a lower delimiting edge and lateral delimiting edges defining a space in the bag. The lower delimiting edge includes a drain valve, whose first drain mouthing in a first hollow element communicates with the space in the bag, and whose second mouthing in a second element is situated outside the delimiting edges of the bag. The drain valve is a disposable valve including a seal between the first and the second element and at least one indicator situated in the area of the seal. A disposable urine bag is provided whereby the drain valve seal may be broken without using significant finger strength and without a risk of the user being soiled with urine.

6 Claims, 5 Drawing Sheets

U.S. PATENT DOCUMENTS

| | | | | |
|---|---|---|---|---|
| 3,187,966 A * | 6/1965 | Klygis | | 222/541.2 |
| 3,204,835 A * | 9/1965 | Michel | | 222/541.5 |
| 3,470,893 A * | 10/1969 | Nelson | | 137/68.11 |
| 3,509,879 A * | 5/1970 | Bathish et al. | | 604/408 |
| 3,519,158 A * | 7/1970 | Anderson | | 215/247 |
| 3,529,599 A * | 9/1970 | Folkman et al. | | 604/323 |
| 3,788,374 A * | 1/1974 | Saijo | | 604/408 |
| 3,858,739 A * | 1/1975 | Turner et al. | | 215/47 |
| 3,986,507 A * | 10/1976 | Watt | | 604/408 |
| 3,993,223 A * | 11/1976 | Welker et al. | | 222/107 |
| 4,195,632 A * | 4/1980 | Parker et al. | | 604/411 |
| 4,228,835 A * | 10/1980 | Robinson et al. | | 604/408 |
| 4,294,247 A * | 10/1981 | Carter et al. | | 604/403 |
| 4,295,495 A * | 10/1981 | Rosemeier et al. | | 138/89 |
| 4,303,067 A * | 12/1981 | Connolly et al. | | 604/408 |
| 4,340,049 A * | 7/1982 | Munsch | | 604/29 |
| 4,410,096 A * | 10/1983 | Paradis | | 215/50 |
| 4,415,393 A * | 11/1983 | Grimes | | 156/244.13 |
| 4,449,971 A * | 5/1984 | Cawood | | 604/544 |
| 4,533,354 A * | 8/1985 | Jensen | | 604/323 |
| 4,703,610 A * | 11/1987 | Bach | | 53/471 |
| 4,936,837 A * | 6/1990 | Wexler et al. | | 604/326 |
| 5,045,067 A * | 9/1991 | Ohnaka et al. | | 604/244 |
| 5,087,251 A | 2/1992 | Heyman et al. | | |
| 5,152,755 A * | 10/1992 | Yoshinori | | 604/256 |
| 5,176,665 A * | 1/1993 | Watanabe et al. | | 604/317 |
| 5,290,105 A * | 3/1994 | Tencati | | 383/203 |
| 5,358,494 A * | 10/1994 | Svedman | | 604/313 |
| 5,417,675 A * | 5/1995 | Watanabe et al. | | 604/317 |
| 5,439,456 A * | 8/1995 | Fabricant | | 604/327 |
| 5,470,324 A | 11/1995 | Cook et al. | | |
| 5,489,281 A * | 2/1996 | Watanabe et al. | | 604/317 |
| 5,496,300 A * | 3/1996 | Hirsch et al. | | 604/327 |
| 5,520,219 A * | 5/1996 | Hessian | | 138/90 |
| 5,643,236 A * | 7/1997 | Hadley | | 604/353 |
| 5,728,087 A | 3/1998 | Niedospial, Jr. | | |
| 5,792,127 A * | 8/1998 | Marran | | 604/353 |
| 5,897,009 A * | 4/1999 | O'Meara | | 215/48 |
| 6,017,598 A * | 1/2000 | Kreischer et al. | | 428/35.4 |
| 6,382,438 B1 * | 5/2002 | Schneider et al. | | 215/48 |
| 6,520,212 B1 * | 2/2003 | Blivet | | 138/96 R |
| 6,887,230 B2 * | 5/2005 | Kubalak et al. | | 604/544 |
| 7,569,262 B2 * | 8/2009 | Szabo et al. | | 428/35.2 |
| 2003/0130646 A1 * | 7/2003 | Kubalak et al. | | 604/544 |

FOREIGN PATENT DOCUMENTS

| | | |
|---|---|---|
| EP | 0 953 322 A2 | 11/1999 |
| EP | 1 219 282 A1 | 7/2002 |
| WO | WO 93/24396 A1 | 12/1993 |
| WO | WO 98/48765 A1 | 11/1998 |
| WO | WO 00/16721 A1 | 3/2000 |
| WO | WO 00/30575 A1 | 6/2000 |

OTHER PUBLICATIONS

Yourdictionary.com—dictionary definition of "surround" http://www.yourdictionary.com/surround accessed Monday, Apr. 2, 2012.*
International Search Report dated Jun. 29, 2004 for International Application No. PCT/DK2004/000128.
International Preliminary Exam Report dated Oct. 29, 2004 for International Application No. PCT/DK2004/000128.

* cited by examiner

DISPOSABLE URINE BAG FOR COLLECTING URINE

This application is the National Stage of International Application No. PCT/DK2004/000128, filed Feb. 26, 2004, which claims priority to Danish Application No. PA 2003 00307, filed Feb. 27, 2003, these references are incorporated herein in their entirety.

BACKGROUND OF THE INVENTION

The invention relates to a disposable urine bag for collecting urine, which bag comprises an upper delimiting edge, a lower delimiting edge and lateral delimiting edges, said edges delimiting a space within the bag, which upper delimiting area is situated at the upper delimiting edge communicates with means outside the bag, and said lower delimiting edge comprising a drain valve, whose first drain mouthing in a first hollow element communicates with the space within the bag, and whose second mouthing in another element is situated outside the delimiting edges of the bag.

In connection with the use of urine bags, such bag comprises a an upper part—typically equipped with a non-return valve whereto a tube is connected which is in turn connected primarily to a catheter. The collection of urine takes place through the catheter tube, and wherein the non-return valve ensures that outflow does not occur through tube and catheter when the bag is filled and turned upside-down. In connection with the manufacture of disposable urine bags, such bag will typically be completely closed at the remaining sides, and therefore the only communication with the exterior takes place through said tube.

Once the bag is filled, a corner will typically be torn off, the bag will be turned, following which it is emptied, and the disposable bag can be disposed of. However, in that connection there is a high risk of the user's fingers being soiled with urine, meaning that there is a risk of cross-contamination in connection with further treatment and, likewise, such urine soiling is unhygienic.

An example of a disposable bag is known from eg U.S. Pat. No. 5,087,251, which comprises an inlet opening for receiving urine and wherein, opposite that, a valve is mounted for sluicing the liquid through. However, that valve is an opening/closing valve that requires quite much finger strength as such and, likewise, its construction is relatively complex and substantially increases the costs in those cases where the bag is used as disposable bag.

It is thus the object of the present invention to provide a disposable urine bag which is not associated with the drawbacks of the prior art systems and whereby it is possible, in a simple manner, to break the seal of the drain valve without having to use significant finger strength and without a risk of the user being soiled with urine.

BRIEF SUMMARY OF THE INVENTION

In one aspect of the invention, this object is accomplished by means of a disposable urine bag for collecting urine, the bag comprising an upper delimiting edge, a lower delimiting edge, and lateral delimiting edges, the edges delimiting a space in the bag, the upper delimiting area situated at the upper delimiting edge communicating with means outside the bag, and the lower delimiting edge comprising a drain valve with a first hollow element and a second element, the second element being situated outside the delimiting edges of the bag, the first hollow element having a first drain mouthing communicating with the space in the bag and a second mouthing located adjacent the second element, and wherein the drain valve is also a disposable valve comprising a seal between the first and the second element and at least one indicator situated in the region of the seal.

When filled with urine and is to be disposed of, the bag will be disconnected from its connection to the catheter. It will subsequently be turned upside-down, and the user will seize the drain valve, the first hollow element of which is at a given distance from the delimiting edge, and wherein the user will press around this hollow element which is manufactured from a through-going flexible material.

Owing to the presence of a seal between the first hollow element located outside the bag and the second element which is also located outside the bag, no liquid is extracted before the indicator situated region of the seal is activated and ruptures the seal. This indicator is preferably configured as an annular radial recess arranged peripherally of the walls of the first element and thus acts as a weakening of the connecting element between the first and the second elements. When the user presses around the first pipe and seizes with the other hand around the second element, on which longitudinal ribs are preferably configured to improve the grip, only little strength is required to twist the second element off the first hollow element, whereby the interior of the first hollow element communicates freely with the external environment. Then the bag can be turned around once again, whereby the drain valve is caused to face downwards, and now the user eases the pressure on the walls of the first hollow element, following which the urine flows out through the hollow element. Precisely because the hollow element has a stud area located externally of the bag, it is ensured that one's fingers are not contaminated with urine. Once the bag is emptied of urine, it may be disposed of.

By providing a disposable urine bag according to one aspect of the invention wherein the seal comprises a plate that blocks the communication of the first hollow element with the second element and wherein the indicator comprises an annular recess, a convenient configuration is obtained of both the seal and the indicator that is to break the seal.

By providing a disposable urine bag in accordance with another aspect the invention wherein the indicator comprises an annular recess with such depth that the delimiting edge thereof corresponds to the location of the inner face of the first hollow element in relation to the centre axis of the valve and wherein the indicator comprises an annular recess whose delimiting bottom is delimited by parts of the periphery of the plate, convenient built-in dimensions between recess and the remaining components are accomplished, whereby the seal is readily ruptured.

By providing a disposable urine bag according to yet another aspect of the invention wherein the indicator comprises an annular recess whose delimiting walls have faces that are essentially parallel to each other and to the delimiting upper and lower faces of the plate, a unequivocal notch effect of the indicator is accomplished whereby a tearing and breaking of the rupture takes place only when the requisite strength is exerted and, likewise, this well-defined configuration ensures that no problems occur in connection with the generation of the recess during moulding as such of the drain valve.

By providing a disposable urine bag according to another aspect of the invention wherein the first hollow element is flexible and has compressible walls, it is enabled to perform a compression of the first hollow element situated outside the delimiting edge, whereby a relative occlusion is accomplished between the seal and the contents of the bag, before the seal is broken.

By providing a disposable urine bag according to yet another aspect of the invention wherein the drain valve is manufactured from a plastics material, a convenient choice of material is accomplished.

The invention will now be explained in further detail with reference to the drawing, wherein

BRIEF DESCRIPTION OF THE DRAWINGS

FIG. 1 shows a disposable urine bag (1) manufactured from two essentially transparent plastics sheets that are, at their peripheries, sealed and connected to each other, preferably by a welding and for providing a space (5) in which the urine may collect. Thus, the seals comprise an upper delimiting edge (2), a lower delimiting edge (3) and lateral delimiting edges (4) that constitute an unbroken line; such, however, that passages are formed at the top and at the bottom, as will be described below. The bag may also comprise other shapes: it may be round, elliptic, etc.

DETAILED DESCRIPTION OF THE INVENTION

Figure 1:
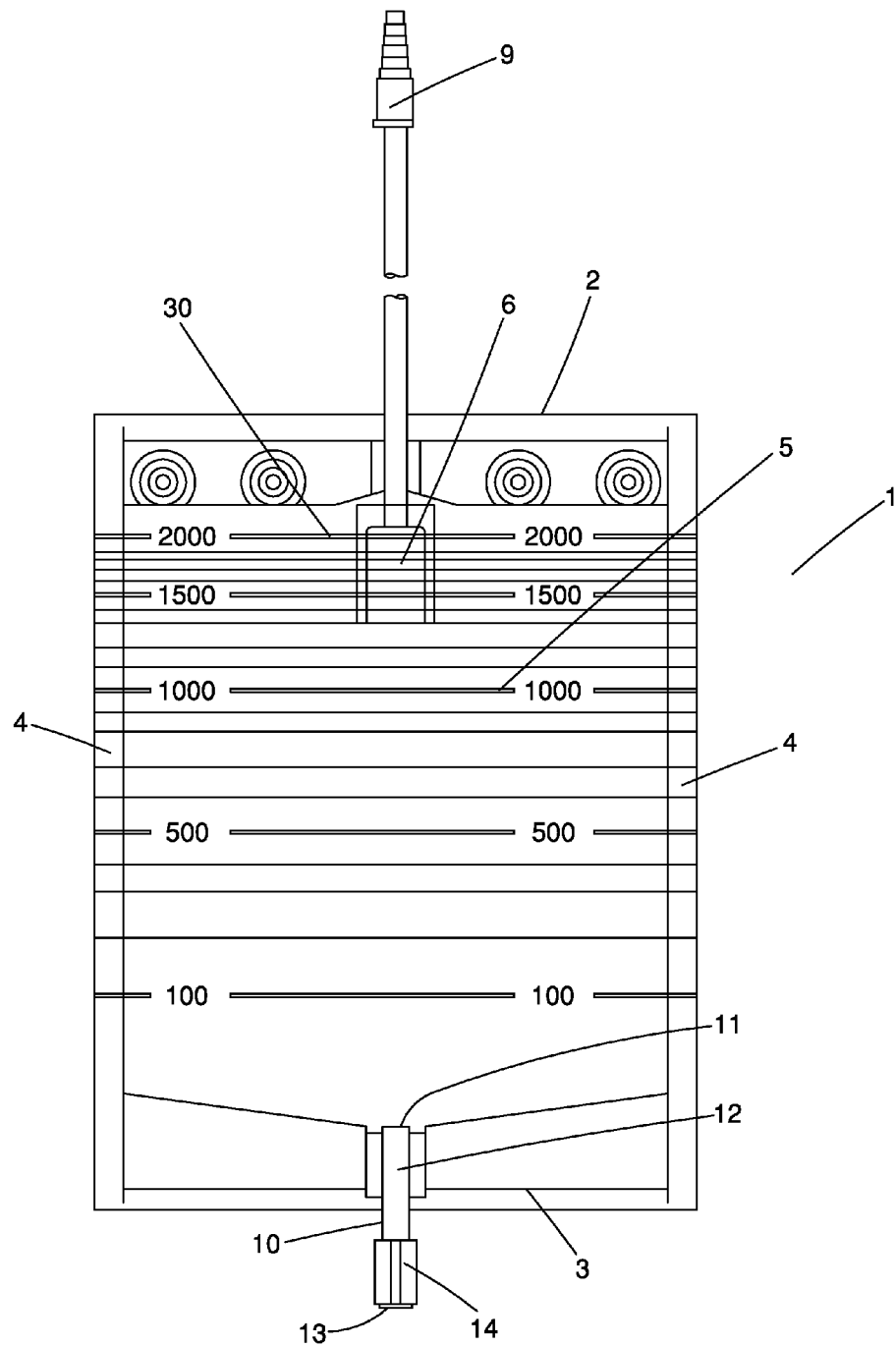
FIG. 1 shows a disposable urine bag comprising a non-return valve connected to outer means in the form of a tube and, opposite that, a drain valve mounted in the bag.

In the upper delimiting area (30) there is, within the bag, provided a non-return valve (6) that ensures that the liquid is able to flow into the bag, when the bag is suspended in straight level and with its drain valve (10) facing downwards; and wherein the non-return valve will prevent outflow of liquid there through, when the bag is reversed to the effect that the drain valve (10) faces upwards. The counter valve (6) is connected to a plastics tube, also referred to herein as means (9) situated externally of the bag. Typically this plastics tubing is connected to a catheter for collecting urine. Opposite the exterior delimiting area (30) there is, at the other end, arranged a drain valve (10) that consists of a first hollow element (12) situated within the bag as such and with passage through the lower delimiting edge, whereby it is connected in a liquid-proof manner to the delimiting edge, and wherein the free end of the first hollow element (12): first drain mouthing (11) is in communication with the space (5). The first hollow element has a smaller section that may correspond to about one third of its length and is situated outside the bag as such and ensuring that the user has a section to seize when the seal of the drain valve is to be broken.

The first hollow element is moulded integrally with a second element (14), which second element (14), in this embodiment, has a larger outer diameter than the first hollow element. In the connecting area between the first element (12) and the second element (14) there is a sealing area (18). The second mouthing (13) of the second element (14) is thus situated outside the bag. That mouthing is not involved in the emptying as such of the bag, as the second element is broken off when the bag is to be emptied.

When emptying is to be performed, the first hollow element is seized. The area outside the urine bag is compressed, while simultaneously the bag is turned such that the drain valve is facing upwards. Then the user seizes around the second element which, in that case, has a larger diameter and further comprises reinforcing ribs (31) and, by a small snapping movement the seal between the first and the second element is broken, following which there is free communication with the space (5) from the exterior, and the user is able to discharge the bag's contents through the passage of the first hollow element.

Figure 2:
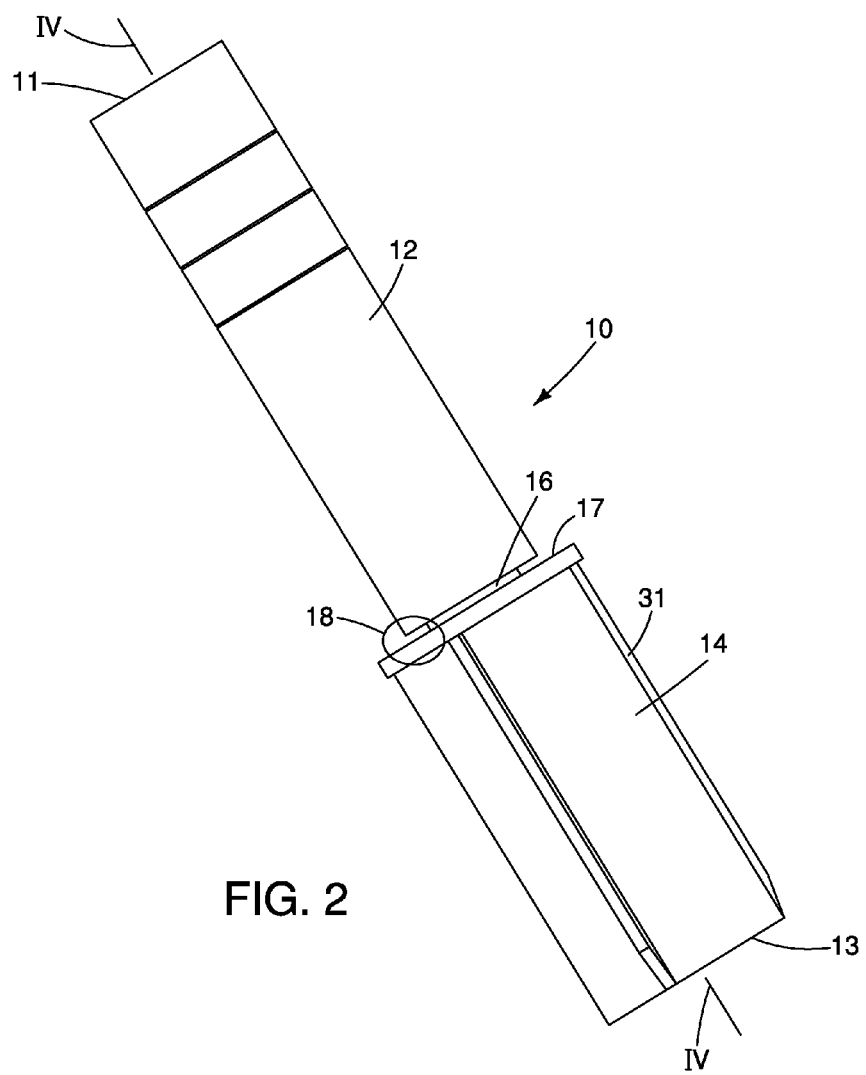
FIG. 2 shows the drain valve shown in FIG. 1 in a detailed view.
Figure 3:
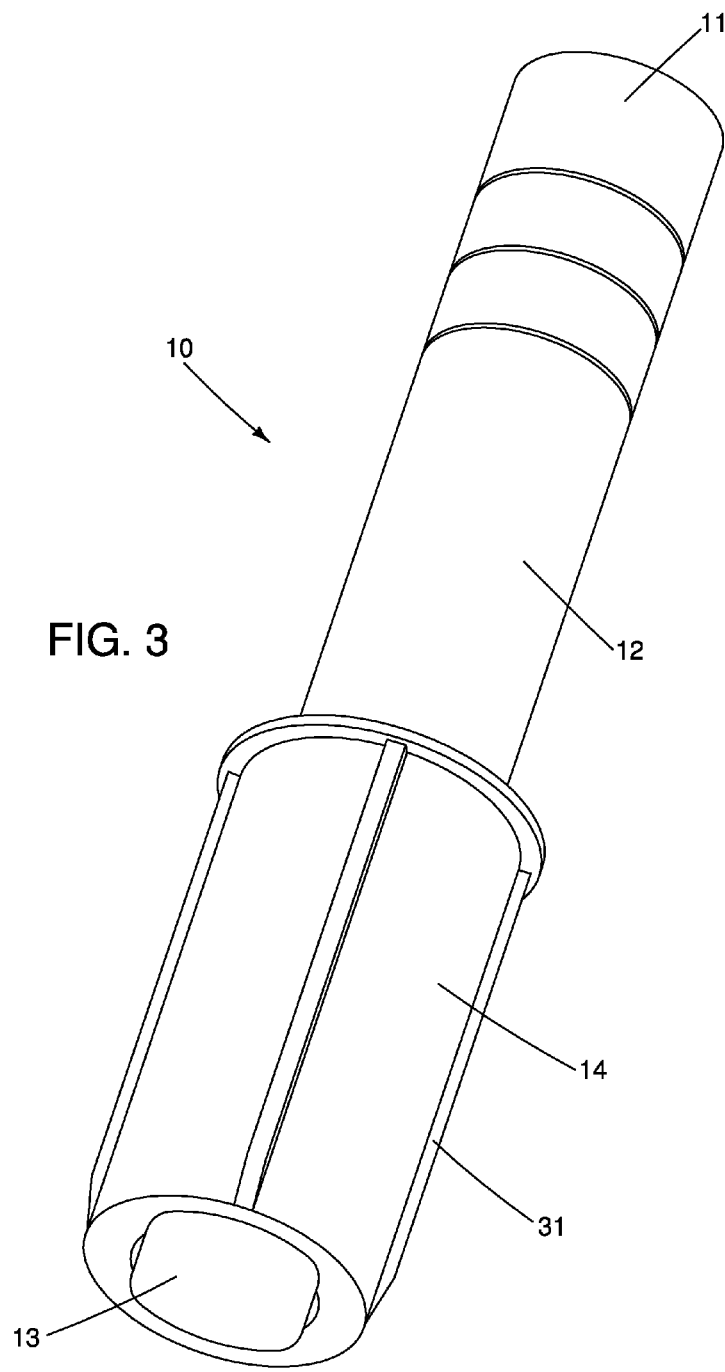
FIG. 3 shows the drain valve shown in FIG. 2, seen in a perspective view.

FIGS. 2 and 3 show a detailed view of the drain valve (10) that thus comprises a first hollow element (12) with an outer diameter of a little less than 9 mm and an inner diameter of a little less than 7 mm and a second element (14) having an outer diameter of a little less than 14 mm and an inner diameter of a little less than 8 mm. Other exemplary embodiments may have other dimensions.

In this context, it is important that the first hollow element is a hollow tube, but as far as the second element is concerned it may very well be solid or configured in other ways. For the sake of process engineering, however, it is preferred that it is also a hollow cylinder. Conveniently, the second element is configured with exterior longitudinally extending reinforcing ribs (31) making gripping more comfortable. Between the first hollow element and the second hollow element a sealing area (18) is provided that comprises a seal (16) between the first and the second element, in such a manner that there is no liquid communication between these elements. Radially of this seal (16) there is at least one indicator (17) in the form of recesses and as will be explained in further detail with reference to FIGS. 4 and 5.

Figure 4:
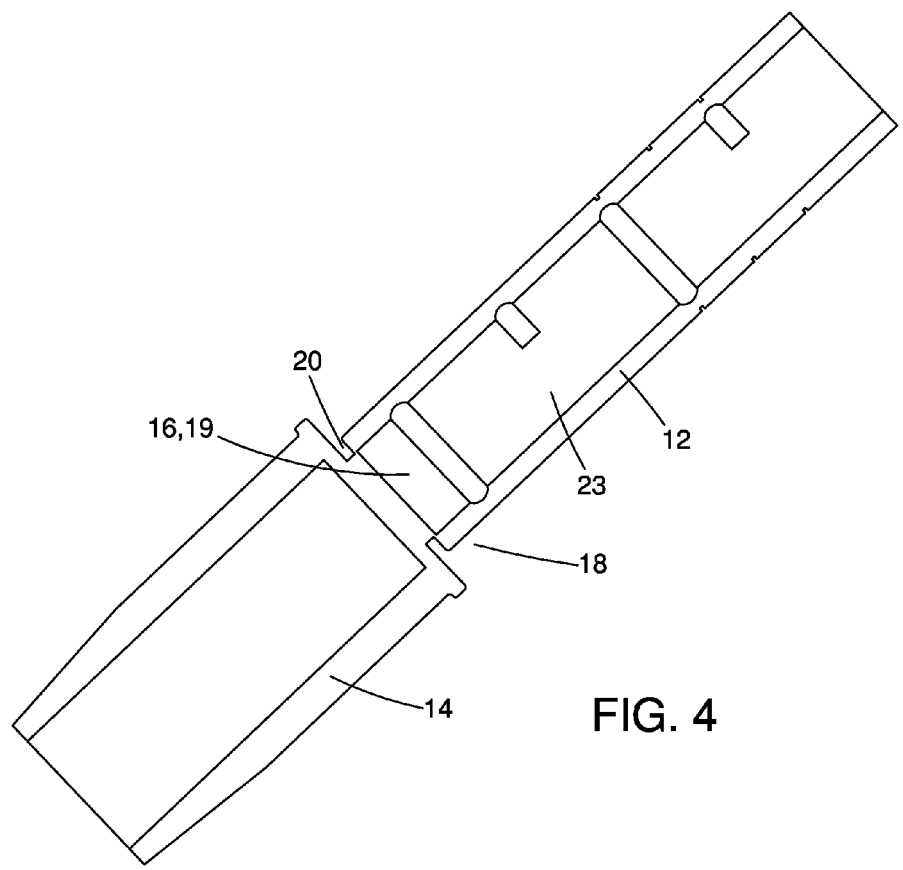
FIG. 4 shows a section along the line IV-IV of FIG. 2.

FIG. 4 is a sectional view through the disclosures of FIG. 2 and showing a first element (12) comprising a hollow tube with an interior face (23) that encloses the hollow communication tube. The second element (14) is also hollow; but, as mentioned above, it might just as well be configured to be solid or the like. The seal (16) between the first and the second element is shown as a plate-shaped seal (19), and in the periphery thereof there is an annularly extending recess (20) in its entire circumference and that acts as rupture indicator between the first and the second element.

The seal can also be provided by the second element being solid and hence constituting a plug that can be broken off by use of little strength due to the indicator.

Figure 5:
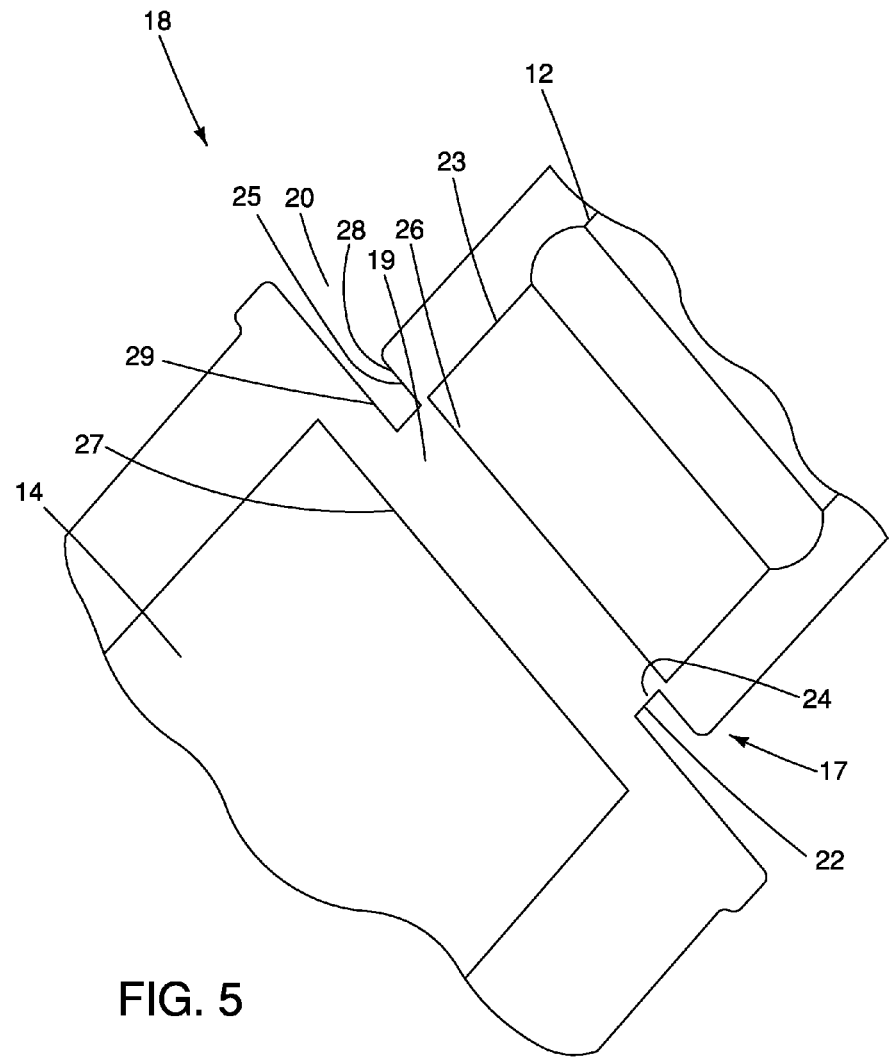
FIG. 5 shows a detailed view of the sealing area.

Thus, FIG. 5 shows the sealing area (18) in an enlarged version, which sealing area is situated between the first element (12) and the second element (14) in the connecting area. The seal comprises a plate 19) with an upper face (26) that forms the bottom of the second mouthing opening of the first tube, and whose lower face (27) forms the lid in the upper area of the second element.

In the periphery of the plate, a recess (20) is configured which is annular throughout the entire periphery of the plate and serving as indicator, which recess is configured with a delimited edge (22), which delimiting edge is in essentially the same level as the inner radial face (23) of the first tube. The recess is further delimited by two flat parallel walls (25) comprising a second wall (29) adjoining the second element and a first wall (28) facing towards the first hollow element, said recess thus being rectangular in cross-section. The distance between the first wall (28) of the recess and the delimiting upper face (26) of the seal is within the area of about 0.2 mm, while the distance from the second wall (29) of the recess and to the delimiting lower face (27) of the seal is within the range of ½-1.5 mm, depending on choice of material and design.

In that context it is important that the indicator has a well-defined shape establishing a notch, thereby preventing unintended tearing of the second element (14) off the first element (12), and likewise it is important in connection with the manufacture of the product that it is possible to manufacture a thin sealing wall in the area that still ensures, however, that leaks do not occur between the first and the second tube.

Preferably the product is intended for manufacture by an injection moulding process, wherein a suitable plastics material is used, eg PVC, and wherein the first element distinguishes itself in being so flexible that it is possible to compress the walls to ensure that the user is able to safely seize around it when the seal is to be broken. This is accomplished by seizing around the second element and breaking the second element from the first element, whereby the seal between the two elements is broken, and the liquid flows out of the space (5) through the first element (12) and out.

The terms first and second elements are to be understood as any design whatsoever, eg circular, oval, triangular, rectangular, and wherein it is essential that the first hollow element is hollow, thereby enabling liquid to pass when the seal is broken, whereas the second element can be hollow or solid.

Disposable urine bag (1)
Upper delimiting edge (2)
Lower delimiting edge (3)
Lateral delimiting edges (4)
Space (5)
Non-return valve (6)
First mouthing (7)
Second mouthing (8)
Means situated outside the bag (9)
Drain valve (10)
First drain mouthing (11)
First hollow element (12)
Second drain mouthing (13)
Second element (14)
Inlet valve (15)
Seal between first and second element (16)
Indicator (17)
Sealing area (18)
Plate (blocking the communication of the first hollow element with the second element) (19)
Annularly extending recess (20)
Depth (21)
Delimiting bottom (22)
Inner radial face (23) of the first hollow element
Parts of the periphery (24) of the plate
Recess delimiting walls (25)
Delimiting upper face (26) of the plate/seal
Delimiting lower face (27) of the plate/seal
First wall of the recess situated towards the first hollow element (28)
Second wall of the recess situated towards the second element (29)
Upper delimiting area (30)
Longitudinally extending ribs (31)

The invention claimed is:

1. A disposable urine bag for collecting urine, said bag comprising an upper delimiting edge, a lower delimiting edge, and lateral delimiting edges, said edges delimiting a space in the bag, the upper delimiting area situated at the upper delimiting edge communicating with means outside the bag, and said lower delimiting edge comprising a single use drain valve with a first hollow element comprising compressible walls being able to stop the flow of urine when pressed against each other and allowing flow of urine when pressure is eased and a second element in extension of said first element, said second element being situated outside the delimiting edges of the bag, said first hollow element having a first drain mouthing communicating with said space in the bag and a second mouthing located adjacent said second element, said second element including a solid plate frangibly and directly connected to said first hollow element at said second mouthing and normally blocking said second mouthing-to define said single use drain valve, said second element with said solid plate being removable from said first element upon said frangible connection being broken to thereby discharge urine at said second mouthing, and an annular recess concentrically surrounding said solid plate.

2. A disposable urine bag according to claim 1, the location of an annular bottom surface of said annular recess corresponds to the location of the inner face of said first hollow element in relation to a centre axis of the valve.

3. The disposable urine bag according to claim 2, wherein the annular recess has delimiting walls with faces that are essentially parallel to each other and to the delimiting upper and lower faces of the plate.

4. A disposable urine bag according to claim 1, wherein the annular recess has delimiting walls with faces that are essentially parallel to each other and to the delimiting upper and lower faces of the plate.

5. A disposable urine bag according to claim 1, wherein the drain valve comprises a plastics material.

6. The disposable urine bag according to claim 1, wherein the compressible walls of the first hollow element are compressible to occlude the valve.

* * * * *